(12) United States Patent
Saito

(10) Patent No.: US 8,738,108 B2
(45) Date of Patent: May 27, 2014

(54) ENDOSCOPE SYSTEM AND PROCESSOR APPARATUS THEREOF, AND METHOD FOR GENERATING IMAGES

(75) Inventor: Takaaki Saito, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 146 days.

(21) Appl. No.: 13/306,693

(22) Filed: Nov. 29, 2011

(65) Prior Publication Data

US 2012/0157803 A1 Jun. 21, 2012

(30) Foreign Application Priority Data

Dec. 21, 2010 (JP) ................................. 2010-284596

(51) Int. Cl.
*A61B 5/1455* (2006.01)
(52) U.S. Cl.
USPC ............ 600/323; 600/310; 600/322; 600/324
(58) Field of Classification Search
USPC ................................................ 600/309–344
See application file for complete search history.

(56) References Cited

U.S. PATENT DOCUMENTS

| 4,914,512 A |   | 4/1990 | Sekiguchi |
| 4,998,973 A | * | 3/1991 | Kikuchi ........................ 600/109 |
| 5,512,940 A | * | 4/1996 | Takasugi et al. ................. 348/71 |

FOREIGN PATENT DOCUMENTS

| JP | 63-311937 A | 12/1988 |
| JP | 06-315477 A | 11/1994 |
| JP | 2648494 B2 | 8/1997 |
| JP | 2005-205195 A | 8/2005 |

OTHER PUBLICATIONS

European Search Report dated Apr. 2, 2012.
Notification of Reasons for Refusal dated Oct. 24, 2012, with English translation.

* cited by examiner

*Primary Examiner* — Eric Winakur
*Assistant Examiner* — Marjan Fardanesh
(74) *Attorney, Agent, or Firm* — McGinn IP Law Group, PLLC

(57) ABSTRACT

An image of a portion to be observed is captured while first light beams are applied thereto. Thereby, a first image signal of a first frame is obtained. The first light beams are in a wavelength range in which an absorption coefficient varies in accordance with a change in oxygen saturation of hemoglobin in blood. An image of the portion to be observed is captured while second light beams are applied thereto. Thereby, a second image signal of a second frame is obtained. The second light beams have a broadband wavelength range. Blood volume and oxygen saturation are obtained from the first and second image signals. A blood volume image representing information on the blood volume in pseudo-color and an oxygen saturation image representing information on the oxygen saturation in pseudo-color are generated. The blood volume image is displayed simultaneously with the oxygen saturation image on a display device.

18 Claims, 15 Drawing Sheets

US 8,738,108 B2

ENDOSCOPE SYSTEM AND PROCESSOR APPARATUS THEREOF, AND METHOD FOR GENERATING IMAGES

BACKGROUND OF THE INVENTION

1. Field of the Invention

The present invention relates to an endoscope system for displaying information on oxygen saturation of hemoglobin in blood and information on blood volume, a processor apparatus of an endoscope system, and a method for generating images.

2. Description Related to the Prior Art

Recently, diagnoses using an endoscope have been performed commonly. In addition to normal observation of a portion of a subject using an endoscope apparatus with illumination of broadband light (white light), special observation using illumination of narrowband light has come into practice. By using the narrowband light, blood vessels in the portion being observed are highlighted in display.

Furthermore, functional information such as oxygen saturation of hemoglobin in blood and blood vessel depth is obtained from an image signal from an endoscope apparatus. The functional information is obtained based on light absorption property of blood vessels and scattering property of a living tissue. Then, an image representing the functional information is generated. For example, in Japanese Patent No. 2648494, colors are assigned according to different oxygen saturation levels. A pseudo-color oxygen saturation image is generated based on the colors assigned. Such oxygen saturation image facilitates finding, for example, a cancer causing the oxygen saturation specifically low. Accordingly, diagnostic performance improves.

Out of cancers causing a low-oxygen or hypoxic condition, an undifferentiated early gastric cancer causes blood density (the blood volume) in a tumor area extremely low compared with well-differentiated cancer. To find the undifferentiated early gastric cancer without fail, it is desired to obtain information on the blood volume from the image signal, in addition to the information on the oxygen saturation. The Japanese Patent No. 2648494, on the other hand, is only capable of obtaining the oxygen saturation. Accordingly, it is difficult to find a lesion site such as the undifferentiated early gastric cancer characterized by both the oxygen saturation and the blood volume.

SUMMARY OF THE INVENTION

An object of the present invention is to provide an endoscope system capable of displaying both information on blood volume and information on oxygen saturation, a processor apparatus of an endoscope system, and a method for generating images.

To achieve the above and other objects, the endoscope system of the present invention includes an illuminating section, an image signal obtaining section, a blood volume and oxygen saturation calculating section, a blood volume and oxygen saturation image generator, and a display section. The illuminating section projects illumination light to a portion to be observed. The portion includes a blood vessel. The image signal obtaining section obtains at least first and second image signals from reflection light reflected from the portion. The reflection light is in a wavelength range from 460 nm to 700 nm. The first image signal is obtained from first reflection light including a wavelength range in which an absorption coefficient varies in accordance with oxygen saturation of hemoglobin in blood. The second image signal is obtained from second reflection light including a wavelength range in which an absorption coefficient varies in accordance with blood volume. The blood volume and oxygen saturation calculating section obtains information on the blood volume and on the oxygen saturation based on the first and second image signals. The blood volume and oxygen saturation image generator generates a blood volume image and an oxygen saturation image. The blood volume image represents the information on the blood volume. The oxygen saturation image represents the information on the oxygen saturation. The display section displays the blood volume image and the oxygen saturation image simultaneously or selectively.

It is preferable that the image signal obtaining section further obtains a third signal as a reference signal to the first and second image signals. The third signal is obtained from third reflection light including an arbitrary wavelength range in the wavelength range from 460 nm to 700 nm.

It is preferable that the blood volume and oxygen saturation image generator has a first color table for blood volume and a second color table for oxygen saturation. The first color table stores pseudo color information varying in accordance with the blood volume. The second color table stores pseudo color information varying in accordance with the oxygen saturation. The images of the blood vessel are generated in pseudo color using the first and second color tables.

It is preferable that one of the first and second color tables varies in chroma and the other varies in hue.

It is preferable that the blood volume and oxygen saturation obtaining section includes a signal ratio calculator, correlation storage, and a calculator. The signal ratio calculator obtains a first signal ratio and a second signal ratio based on the first to third image signals. The first signal ratio depends on the blood volume. The second signal ratio depends on both the blood volume and the oxygen saturation. The correlation storage stores a first correlation between the blood volume and the first signal ratio and a second correlation between the oxygen saturation and the first and second signal ratios. The calculator obtains the information on the blood volume from the first correlation and the information on the oxygen saturation from the second correlation. The blood volume corresponds to the first signal ratio. The oxygen saturation corresponds to the second signal ratio.

It is preferable that the image signal obtaining section has a color image sensor provided with R, G, and B color filters on its imaging surface.

It is preferable that the illuminating section projects light, having a wavelength range in which the absorption coefficient varies in accordance with a change in the oxygen saturation of hemoglobin in blood, as the illumination light to the portion to obtain the first image signal. The illuminating section projects white light as the illumination light to obtain the second and third image signals.

It is preferable that the white light is pseudo white light generated by applying excitation light having a predetermined wavelength to a phosphor.

It is preferable that the illuminating section projects white light as the illumination light to the portion to obtain the first to third image signals.

It is preferable that the white light is pseudo white light generated by applying excitation light having a predetermined wavelength to a phosphor.

It is preferable that the illuminating section successively projects light in a wavelength range from 460 nm to 480 nm, light in a wavelength range from 540 nm to 580 nm, and light in a wavelength range from 590 nm to 700 nm as the illumination light.

It is preferable that the light in each of the wavelength ranges is generated by filtering white light with a narrowband filter.

It is preferable that the illuminating section simultaneously projects light in a wavelength range from 460 nm to 480 nm and light in a wavelength range from 540 nm to 700 nm as the illumination light.

It is preferable that the illuminating section successively projects light in a wavelength range from 530 nm to 550 nm, light in a wavelength range from 555 nm to 565 nm, and light in a wavelength range from 590 nm to 700 nm as the illumination light.

It is preferable that the light in each of the wavelength ranges is generated by filtering white light with a narrowband filter.

A processor apparatus used with an endoscope includes a receiving section, a blood volume and oxygen saturation calculating section, and a blood volume and oxygen saturation image generator. The receiving section receives the first and second image signals from the endoscope. The blood volume and oxygen saturation calculating section obtains information on the blood volume and on the oxygen saturation based on the first and second image signals. The blood volume and oxygen saturation image generator generates a blood volume image and an oxygen saturation image. The blood volume image represents the information on the blood volume. The oxygen saturation image represents the information on the oxygen saturation.

A method for generating images comprising a projecting step, an image signal obtaining step, an information obtaining step, and a generating step. In the projecting step, illumination light is projected to a portion to be observed. The portion includes a blood vessel. In the image signal obtaining step, at least first and second image signals are obtained from reflection light reflected from the portion. The reflection light is in a wavelength range from 460 nm to 700 nm. The first image signal is obtained from first reflection light including a wavelength range in which an absorption coefficient varies in accordance with oxygen saturation of hemoglobin in blood. The second image signal is obtained from second reflection light including a wavelength range in which an absorption coefficient varies in accordance with blood volume. In the information obtaining step, information on the blood volume and on the oxygen saturation is obtained based on the first and second image signals. In the generating step, a blood volume image and an oxygen saturation image are generated. The blood volume image represents the information on the blood volume. The oxygen saturation image represents the information on the oxygen saturation.

According to the present invention, the blood volume image representing the information on the blood volume and the oxygen saturation image representing the information on the oxygen saturation can be displayed. Thereby, it becomes easy to find a lesion site.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
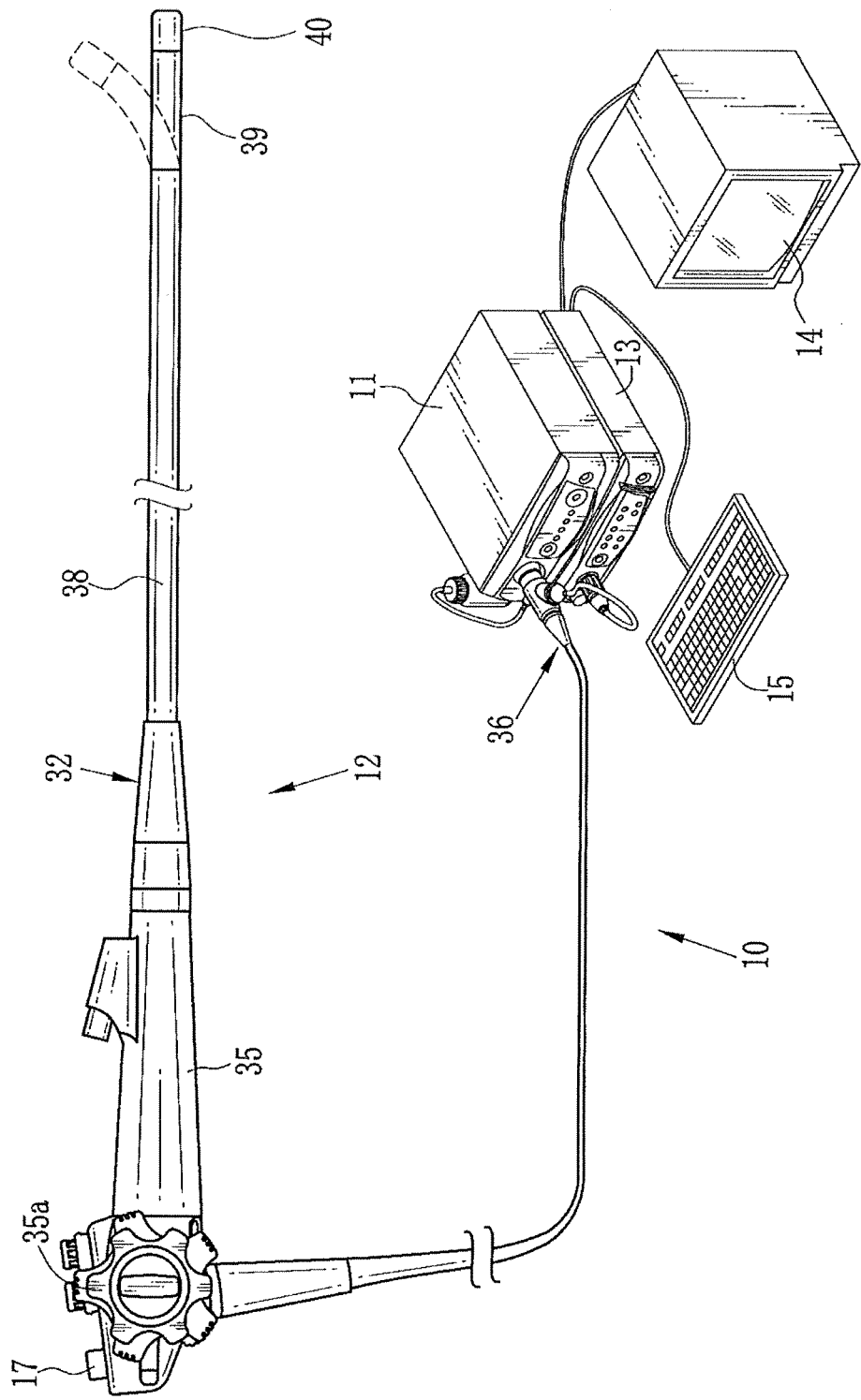
FIG. 1 is an external view of an endoscope system of a first embodiment.
Figure 2:
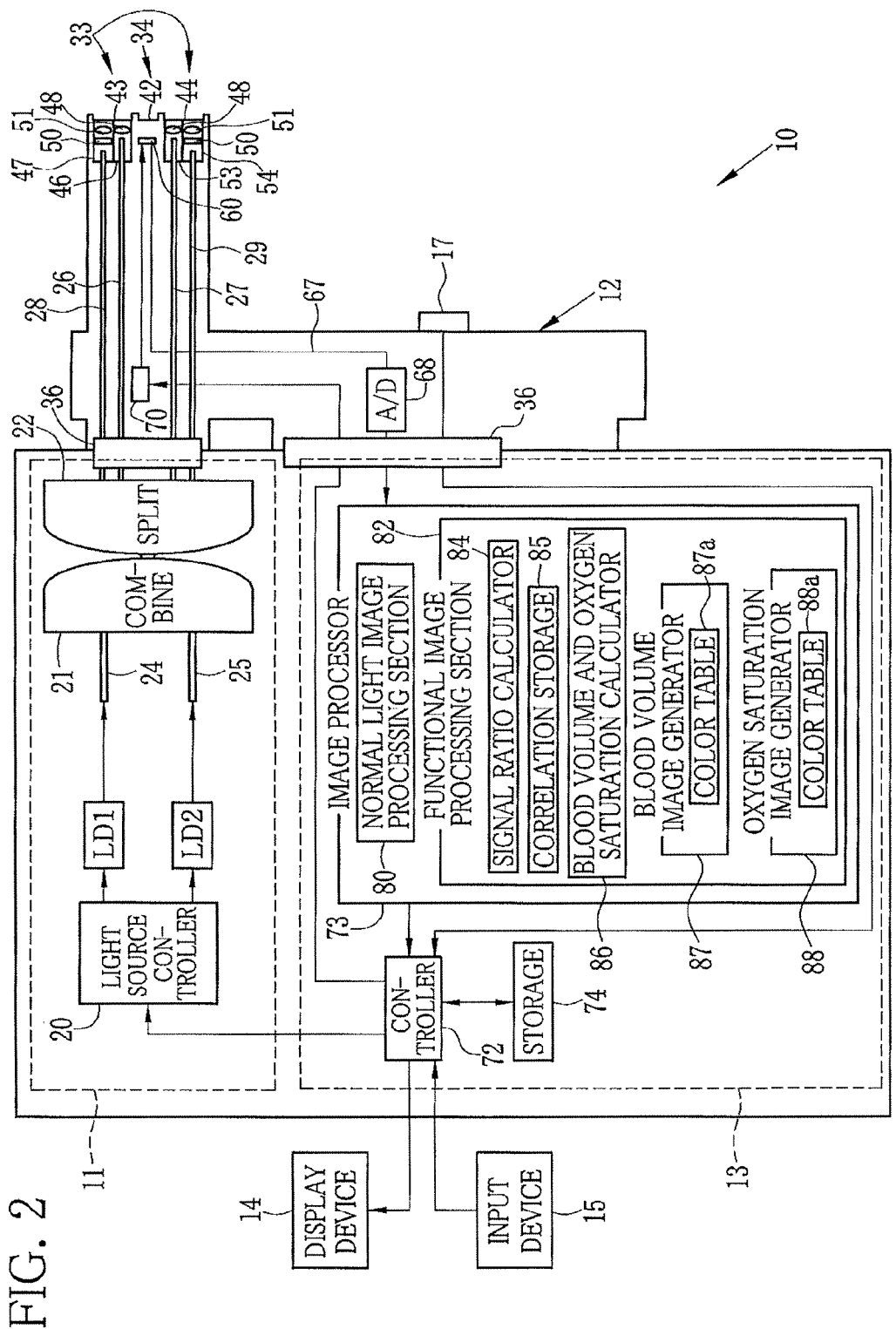
FIG. 2 is a block diagram showing a configuration of an endoscope system.

In FIGS. 1 and 2, an endoscope system 10 of a first embodiment is provided with a light source apparatus 11, an endoscope apparatus 12, a processor apparatus 13, a display device 14, and an input device 15. The light source apparatus 11 generates light in a predetermined wavelength range. The endoscope apparatus 12 guides the light from the light source apparatus 11 and applies the light as illumination light to a portion to be observed (hereinafter referred to as the target portion) of a subject. The endoscope apparatus 12 captures an image of the light reflected from the target portion and the like. The processor apparatus 13 performs image processing to an image signal obtained with the endoscope apparatus 12. The display device 14 displays an endoscopic image and the like from the processor apparatus 13. The input device 15 includes a keyboard, for example.

The endoscope system 10 has two observation modes: a normal light mode and a functional information mode. In the normal light mode, a normal light image is displayed on the display device 14. The normal light image is a subject image of visible light in a wavelength range from blue to red. In the functional information mode, an oxygen saturation image and a blood volume image are displayed on the display device 14. The oxygen saturation image is a pseudo color image showing information on oxygen saturation of hemoglobin in blood in blood vessel(s) included in the target portion. The blood volume image is a pseudo color image showing information on blood volume in blood vessel(s) included in the target portion. The observation mode is switched as necessary based on a command inputted from a selection switch 17 of the endoscope apparatus 12 or the input device 15, for example.

The light source apparatus 11 is provided with two kinds of laser light sources LD1 and LD2, a light source controller 20, a combiner 21, and a splitter 22. The laser light source LD1 generates narrowband light beams (oxygen saturation measuring beams) used for measuring the oxygen saturation. The laser light source LD2 applies excitation light beams to a phosphor 50, placed at a front end of the endoscope apparatus 12, to generate white light (pseudo white light). The light beams from the laser light source LD1 are incident on an optical fiber 24 through a condenser lens (not shown). The light beams from the laser light source LD2 are incident on an optical fiber 25 through a condenser lens (not shown). For each of the laser light sources LD1 and LD2, a broad area InGaN laser diode, an InGaNAs laser diode, or a GaNAs laser diode can be used, for example.

The light source controller 20 controls the laser light sources LD1 and LD2 to adjust emission timing of each of the laser light sources LD1 and LD2 and a light quantity ratio between the laser light sources LD1 and LD2. In this embodiment, in the normal light mode, the laser light source LD1 is turned off and the laser light source LD2 is turned on. On the other hand, in the functional information mode, the laser light sources LD1 and the LD2 are turned on alternately at predetermined time intervals.

The combiner 21 combines the light beams from the optical fiber 24 and the light beams from the optical fiber 25. The splitter 22 splits the combined light beams into four paths. Out of the four paths of light beams, the light beams from the laser light source LD1 are transmitted through light guides 26 and 27. The light beams from the laser light source LD2 are transmitted through light guides 28 and 29. Each of the light guides 26 to 29 is composed of a bundle fiber that is a plurality of optical fibers bundled together. Note that the light beams from the laser light sources LD1 and LD2 may be directly incident on the light guides 26 to 29 without using the combiner 21 and the splitter 22.

The endoscope apparatus 12 is composed of an electronic endoscope and is provided with a scope 32, an illuminating section 33, an imaging section 34, an operation section 35, and a connector section 36. The illuminating section 33 applies the four paths of light beams transmitted through the respective light guides 26 to 29 to the target portion. The imaging section 34 captures an image of the target portion. The operation section 35 is used for bending an end portion of the scope 32 and for performing operation for observation. The connector section 36 connects the scope 32, the light source apparatus 11, and the processor apparatus 13 in a detachable manner.

The scope 32 is provided with a flexible portion 38, a bending portion 39, and a distal portion 40 in this order from the operation section 35 side. The flexible portion 38 is flexible inside the subject when the scope 32 is inserted into the subject. The bending portion 39 is bent by rotating an angle knob 35a disposed in the operation section 35. The bending portion 39 can be bent at any angle in a vertical or horizontal direction to direct the distal portion 40 to the target portion.

The distal portion 40 is provided with the illuminating section 33 and the imaging section 34. The imaging section 34 is provided with a capture window 42 substantially at the center of the distal portion 40. The capture window 42 passes the light reflected from the target portion and the like. The illuminating section 33 includes two illumination windows 43 and 44 provided on respective sides of the imaging section 34. Each of the illumination windows 43 and 44 projects two types of light, the oxygen saturation measuring beams and the white light, to the target portion.

Two projection units 46 and 47 are disposed behind the illumination window 43. The projection unit 46 projects the oxygen saturation measuring beams from the light guide 26 to the target portion through a lens 48. The projection unit 47 applies the excitation light beams from the light guide 28 to the phosphor 50 to project white light. The white light is projected to the target portion through a lens 51. Similarly, projection units 53 and 54 are disposed behind the illumination window 44. The projection unit 53 is similar to the projection unit 46. The projection unit 54 is similar to the projection unit 47.

Figure 3:
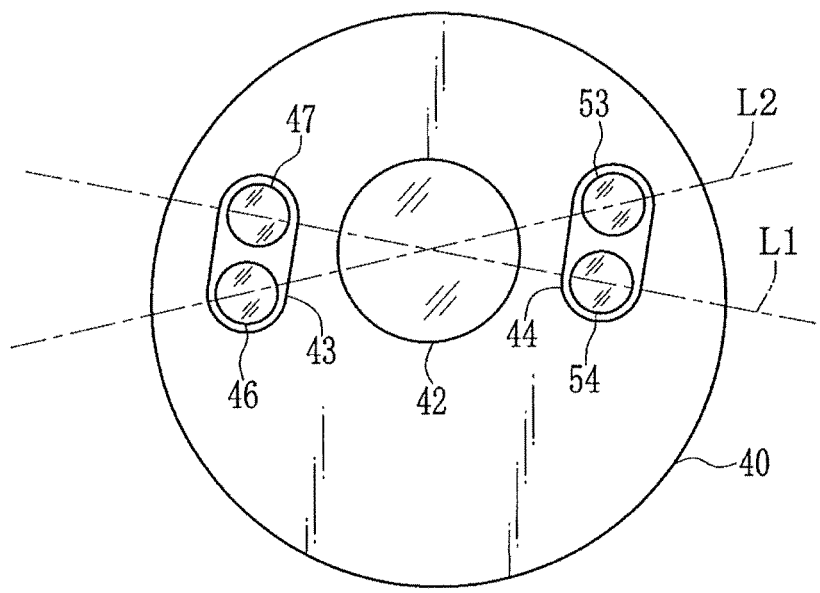
FIG. 3 is a front view of a distal portion.

As shown in FIG. 3, in the distal portion 40, the capture window 42 is disposed between the illumination windows 43 and 44. The four projection units 46, 47, 53, and 54 are arranged such that long and short dashed lines L1 between the output surfaces of the projection units 47 and 54 and long and short dashed lines L2 between the output surfaces of the projection units 46 and 53 cross each other at a center portion of the capture window 42. This arrangement prevents unevenness in illumination. Each of the projection units 47 and 54 is provided with the phosphor 50. The projection units 46 and 53 are not provided with the phosphor 50.

The plate-like phosphor 50 includes several kinds of fluorescent substances, for example, YAG fluorescent substances or BAM ($BaMgAl_{10}O_{17}$). These fluorescent substances absorb a part of the excitation light beams from the laser light source LD2 to emit green to yellow light (fluorescence). When the excitation light is applied to the phosphor 50, the green to yellow fluorescence emitted from the phosphor 50 and the excitation light, passed through the phosphor 50 without being absorbed, are combined to generate the white light (pseudo white light). The phosphor may be referred to as Micro White (registered trademark)

Figure 4:
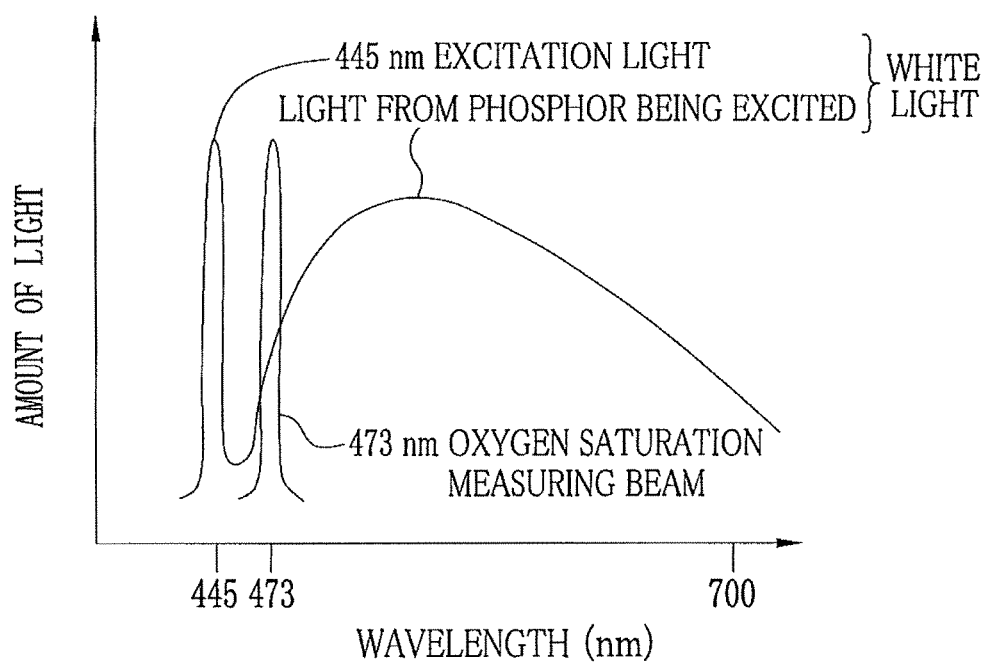
FIG. 4 is a graph showing emission spectra of oxygen saturation measuring beams and white light.

Accordingly, as shown in FIG. 4, the white light emitted from each of the projection units 47 and 54 (each having the phosphor 50) has an emission spectrum including a wavelength range of the excitation light having the center wavelength of 445 nm and a wavelength range approximately from 450 nm to 700 nm in which emission intensity of the fluorescence generated by the excitation light increases. On the other hand, the oxygen saturation measuring beams emitted from each of the projection units 46 and 53 (neither having the phosphor 50) has an emission spectrum in a wavelength range around the center wavelength of 473 nm.

The white light of the present invention does not necessarily include all wavelength components of the visible light. Like the above pseudo white light, the white light only needs to include light in a specific wavelength range, for example, light of a primary color, R (red), G (green), or B (blue). In other words, the white light may include light having the wavelength components from green to red or light having the wavelength components from blue to green, for example.

An objective lens unit (not shown) is provided behind the capture window 42. The objective lens unit takes in light (image light) reflected from the target portion of the subject.

An image sensor 60 is provided behind the objective lens unit. The image sensor 60 is a CCD (charge coupled device) or a CMOS (complementary metal-oxide semiconductor), for example. The image sensor 60 receives the image light of the target portion to generate an image thereof.

A light receiving surface (imaging surface) of the image sensor 60 receives the light from objective lens unit. Then the image sensor 60 photoelectrically converts the light to output an imaging signal (analog signal). The image sensor 60 is a color CCD. On the light receiving surface, three kinds of pixels, R pixels each provided with a red color filter, G pixels each provided with a green color filter, and B pixels each provided with a blue color filter are arranged in a matrix with a predetermined pattern.

Figure 5:
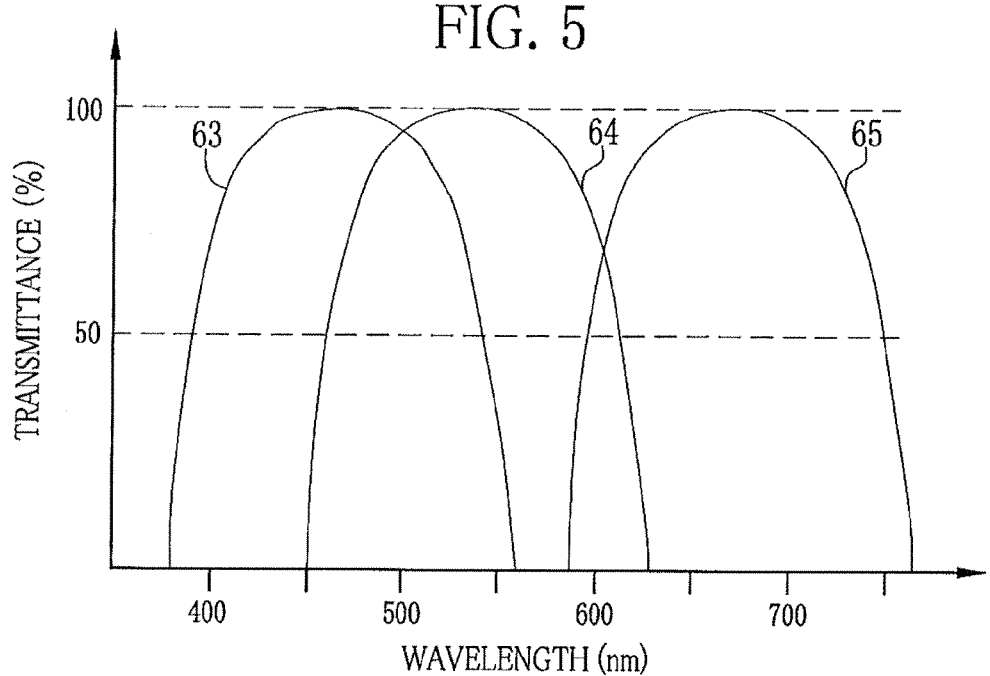
FIG. 5 is a graph showing spectral characteristic of R, G, and B color filters.

As shown in FIG. 5, the blue color filter has spectral characteristic 63. The green color filter has spectral characteristic 64. The red color filter has spectral characteristic 65. Accordingly, out of the light reflected from the target portion, the white light passes through all of the red, green, and blue color filters. Thereby, a color signal is outputted from each of the R, G, and B pixels of the image sensor 60. On the other hand, because the center wavelength of the oxygen saturation measuring beams is 473 nm, the B pixel mainly outputs the color signal.

A three-color signal, being the imaging signal (analog signal) outputted from the image sensor 60, is inputted to an A/D converter 68 through a scope cable 67. The A/D converter 68 converts the imaging signal into an image signal (digital signal) corresponding to a voltage level of the imaging signal. After the conversion, the image signal is inputted to an image processor 73 of the processor apparatus 13 through the connector section 36.

Figure 6A:
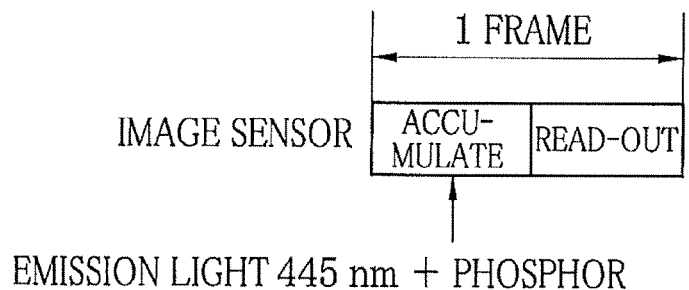
FIG. 6A is an explanatory view showing operation of an image sensor in a normal light mode.

An imaging controller 70 controls imaging of the image sensor 60. As shown in FIG. 6A, in the normal light mode, two steps, an accumulation step and a read-out step are performed in a single frame period. In the accumulation step, electric charge obtained by the photoelectric conversion of the white light (445 nm+phosphor) is accumulated. In this embodiment, the white light (445 nm+phosphor) denotes that the white light is generated by applying the excitation light at 445 nm to the phosphor 50. In the read-out step, the electric charge accumulated is read out. The accumulation step and the read-out step are repeated alternately in the normal light mode.

Figure 6B:
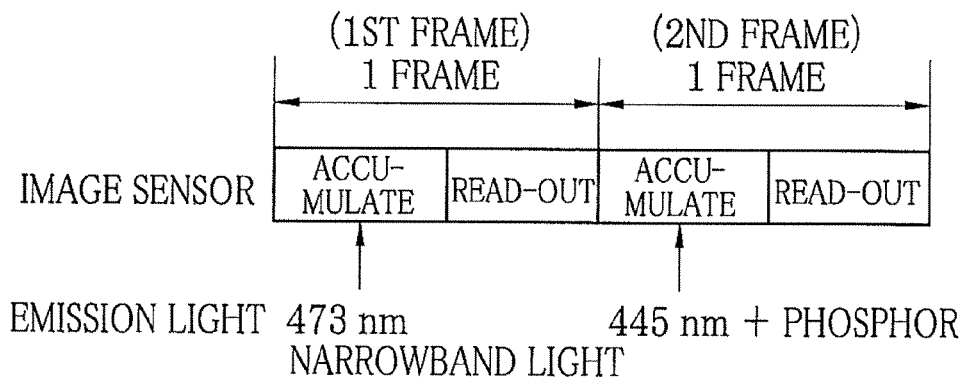
FIG. 6B is an explanatory view showing operation of the image sensor in a functional information mode.

On the other hand, in the functional information mode as shown in FIG. 6B, for the first frame, two steps, an accumulation step and a read-out step are performed in a single frame period. In the accumulation step, the electric charge obtained by photoelectric conversion of the oxygen saturation measuring beams (the narrowband light at 473 nm) is accumulated. In the read-out step, the electric charge accumulated is read out. Next, for the second frame, two steps, an accumulation step and a read-out step are performed. In the accumulation step, the electric charge obtained by photoelectric conversion of the white light (445 nm+Micro White) is accumulated. In the read-out step, the electric charge accumulated is read out. This imaging control using two frames is repeated in the functional information mode.

The image signal of the first frame is composed of a blue signal (B signal) B1 from the B pixel of the image sensor 60, a green signal (G signal) G1 from the G pixel of the image sensor 60, and a red signal (R signal) R1 from the R pixel of the image sensor 60. The image signal of the second frame is the same as the normal light image signal. The image signal of the second frame is composed of a B signal B2 from the B pixel, a G signal G2 from the G pixel, and an R signal R2 from the R pixel.

Through the operation section 35 and the scope 32 of the endoscope apparatus 12, various channels (not shown) are provided. The channels include, for example, an air/water channel and a forceps channel through which a sample collecting device or the like is inserted.

The processor apparatus 13 is provided with a controller 72, the image processor 73, and storage 74. The controller 72 is connected to the display device 14 and the input device 15. The controller 72 controls operations of the image processor 73, the light source controller 20 of the light source apparatus 11, the imaging controller 70 of the endoscope apparatus 12, and the display device 14, according to a command instructing the observation mode and the like. The command is issued from the selection switch 17 or the input device 15 of the endoscope apparatus 12.

The image processor 73 is provided with a normal light image processing section 80 and a functional image processing section (blood volume and oxygen saturation calculating section) 82. The image processor 73 performs predetermined image processing to the image signal from the endoscope apparatus 12. The normal light image processing section 80 performs predetermined image processing to the image signal to generate a normal light image.

The functional image processing section 82 calculates information on the blood volume and on the oxygen saturation of hemoglobin in blood of the target portion based on the image signal inputted from the endoscope apparatus 12. The functional image processing section 82 generates a blood volume image showing the blood volume in pseudo color and an oxygen saturation image showing the oxygen saturation in pseudo color. The functional image processing section 82 is provided with a signal ratio calculator 84, correlation storage 85, a blood volume and an oxygen saturation calculator 86, a blood volume image generator 87, and an oxygen saturation image generator 88.

The signal ratio calculator 84 calculates a signal ratio between the image signal of the first frame and the image signal of the second frame obtained in the functional information mode, relative to picture elements located at the same positions or coordinates in the first and second frames. The signal ratio is calculated for every picture element in the image signal. In this embodiment, the signal ratio calculator 84 calculates a signal ratio B1/G2 between the B signal B1 of the first frame and the G signal G2 of the second frame, and a signal ratio R2/G2 between the R signal R2 of the second frame and the G signal G2 of the second frame. The signal ratios may be calculated only for the picture elements in vascular portions of the image signals. In this case, the vascular portion is determined based on a difference between an image signal of the vascular portion and an image signal of a portion other than the vascular portion.

Figure 7:
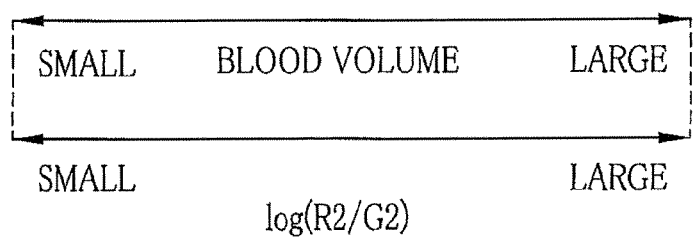
FIG. 7 is a graph showing a correlation between blood volume and a signal ratio R2/G2.

The correlation storage 85 stores a correlation between the signal ratio R2/G2 and the blood volume, and a correlation between the oxygen saturation and the signal ratios B1/G2 and R2/G2. As shown in FIG. 7, the correlation between the signal ratio and the blood volume is stored in a one-dimensional table. The correlation is defined or determined such that the signal ratio R2/G2 increases with the blood volume. The signal ratio R2/G2 is stored in log scale.

Figure 8:
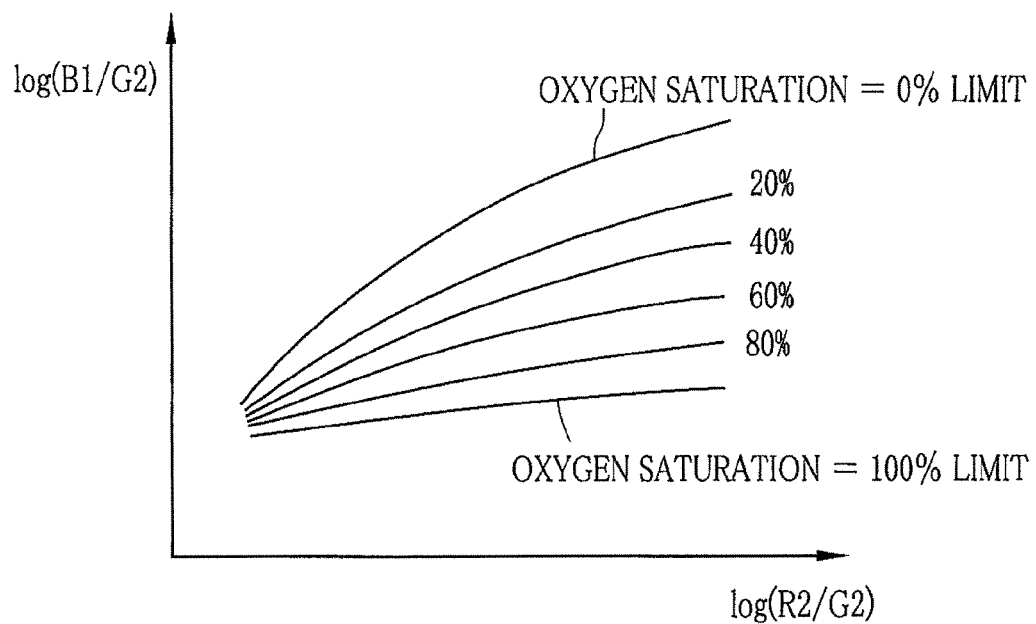
FIG. 8 is a graph showing a correlation between oxygen saturation and signal ratios B1/G2 and R2/G2.

On the other hand, as shown in FIG. 8, the correlation between the signal ratios and the oxygen saturation is stored in a two dimensional table. The two dimensional table defines contour lines of the oxygen saturation on a two dimensional space. The positions and shapes of the contour lines are obtained by physical simulation of light scattering, and vary according to the blood volume. For example, a space between the contour lines increases or decreases when there is a change in the blood volume. Here, the signal ratios B1/G2 and R2/G2 are stored in log scale.

Figure 9:
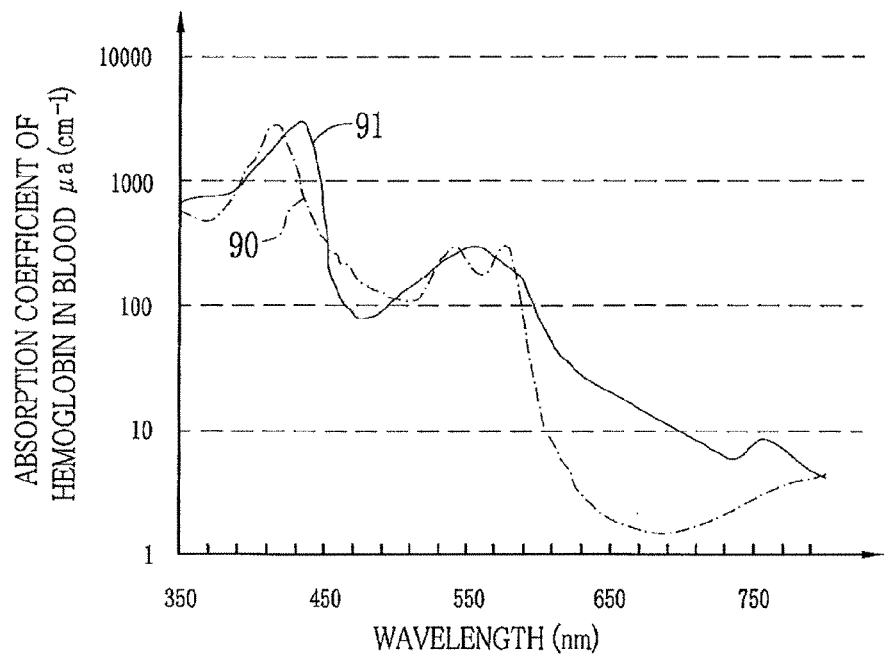
FIG. 9 is a graph showing absorption coefficients of hemoglobin.

The above-described correlations are closely related to light absorption property and light scattering property of oxyhemoglobin and deoxyhemoglobin shown in FIG. 9. In FIG. 9, a characteristic line 90 shows an absorption coefficient of oxyhemoglobin. A characteristic line 91 shows an absorption coefficient of deoxyhemoglobin. As shown in FIG. 9, it is easy to obtain information on the oxygen saturation at 473 nm, for example, where a difference between the absorption coefficient of the oxyhemoglobin and the absorption coefficient of the deoxyhemoglobin is large. However, the B signal including a signal of the light at 473 nm is highly dependent on both the oxygen saturation and the blood volume. To obtain the oxygen saturation accurately without depending on the blood volume, the signal ratios B1/G2 and R2/G2 are used in addition to the B signal B1. The signal ratios B1/G2 and R2/G2 are obtained from the B signal B1, the R signal R2, and the G signal G2. The R signal R2 corresponds to the light which varies depending mainly on the blood volume. The G signal G2 is a reference signal for the B signal B1 and the R signal R2.

Based on wavelength dependence of the absorption coefficient of hemoglobin in blood, there are three important points.
1. In a wavelength range close to 470 nm, for example, in a blue wavelength range with the center wavelength of 470 nm±10 nm, the absorption coefficient varies significantly in accordance with a change in the oxygen saturation.
2. When averaged in a green wavelength range from 540 nm to 580 nm, the absorption coefficient is likely to be unaffected by the oxygen saturation.
3. In a red wavelength range from 590 nm to 700 nm, the absorption coefficient appears to vary significantly in accordance with a change in the oxygen saturation. Actually, however, the absorption coefficient is likely to be unaffected by the oxygen saturation because the value of the absorption coefficient is extremely small.

The blood volume and the oxygen saturation calculator 86 obtains both the blood volume and the oxygen saturation in each picture element using the correlations stored in the correlation storage 85 and the signal ratios B1/G2 and R2/G2 obtained by the signal ratio calculator 84. In the one-dimensional table in the correlation storage 85, the blood volume is a value corresponding to the signal ratio R2/G2 obtained by the signal ratio calculator 84. To obtain the oxygen saturation, as shown in FIG. 10, first, a point P corresponding to the signal ratios B1*/G2* and R2*/G2*, obtained by the signal ratio calculator 84, is determined in the two-dimensional space.

Figure 10:
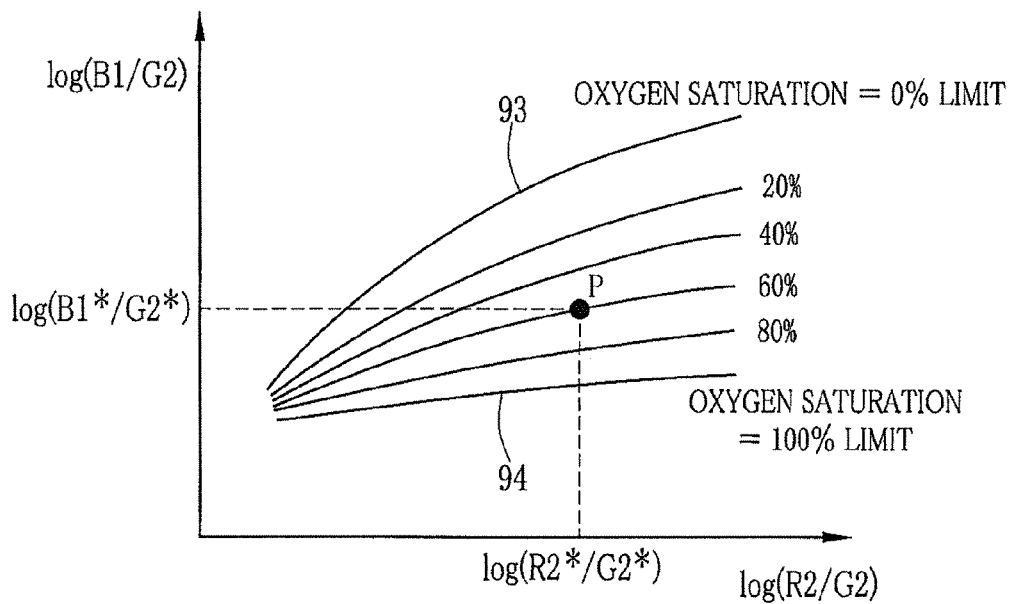
FIG. 10 is a graph describing how to determine the oxygen saturation from the signal ratio with the use of the graph of FIG. 8.

As shown in FIG. 10, when the point P is positioned between a lower limit line 93 (the oxygen saturation=0% limit) and an upper limit line 94 (the oxygen saturation=100% limit), the percentage of the oxygen saturation is the percentage expressed by the contour line where the point P is positioned. For example, in FIG. 10, the point P is positioned on the contour line of "60%", so the percentage of the oxygen saturation is 60%. If the point P is positioned outside of a range between the lower limit line 93 and the upper limit line 94, for example, when the point P is positioned above the lower limit line 93, the oxygen saturation is determined to be 0%. When the point P is positioned below the upper limit line 94, the oxygen saturation is determined to be 100%. Note that when the point P is positioned outside of a range between the lower limit line 93 and the upper limit line 94, the reliability of the oxygen saturation in the picture element may be reduced so as not to display the oxygen saturation.

The blood volume image generator 87 generates a blood volume image showing the blood volume, calculated by the blood volume and the oxygen saturation calculator 86, in pseudo-color. The blood volume image is composed of a video signal. The video signal includes luminance Y and color difference signals Cb and Cr. The G signal G2 of the normal light image signal is assigned to the luminance Y. The G signal G2 corresponds to the reflected light in a wavelength range in which the light absorption by the hemoglobin is rather large. Accordingly, the image generated based on the G signal G2 allows visible observation of blood vessels and surface unevenness of mucosa, for example. By assigning the G signal G2 to the luminance Y, overall brightness of the pseudo color image is defined or determined.

Figure 11:
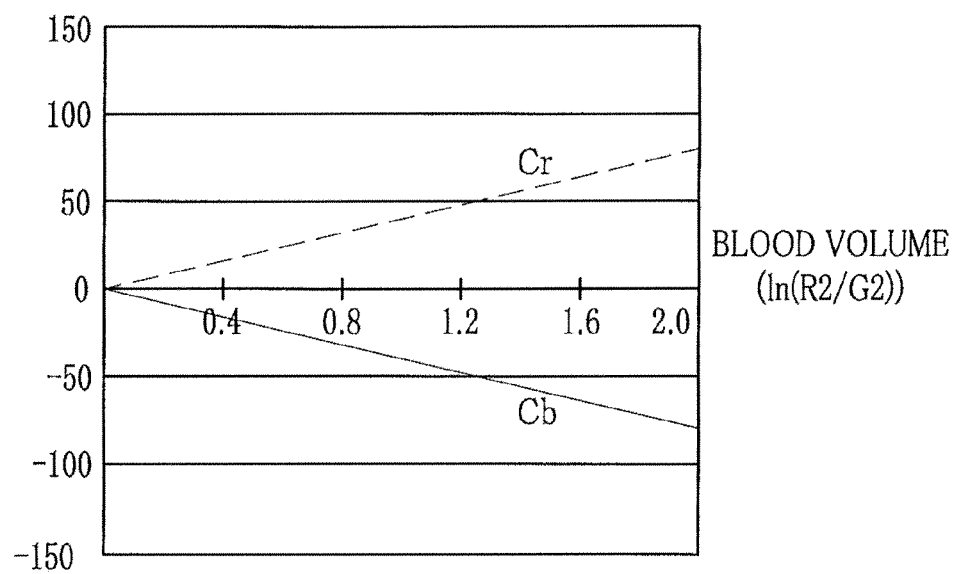
FIG. 11 is a graph showing a relation between the blood volume and color difference signals.

On the other hand, according to a color table 87a, signal values corresponding to the blood volume are assigned to the color difference signals Cb and Cr, respectively. As shown in FIG. 11, in the color table 87a, the signal value of the color difference signal Cb decreases as the blood volume increases. Conversely, the signal value of the color difference signal Cr increases as the blood volume increases. Accordingly, redness of the blood volume image increases as the blood volume increases. The redness decreases in chroma and becomes closer to monochromatic as the blood volume decreases.

The oxygen saturation image generator 88 generates the oxygen saturation image showing the oxygen saturation, obtained by the blood volume and the oxygen saturation calculator 86, in pseudo color. The oxygen saturation image is composed of a video signal. The video signal includes luminance Y and color difference signals Cb and Cr. The G signal G2 of the normal light image signal is assigned to the luminance Y. According to a color table 88a, signal values corresponding to the oxygen saturation are assigned to the color difference signals Cb and Cr, respectively.

Figure 12:
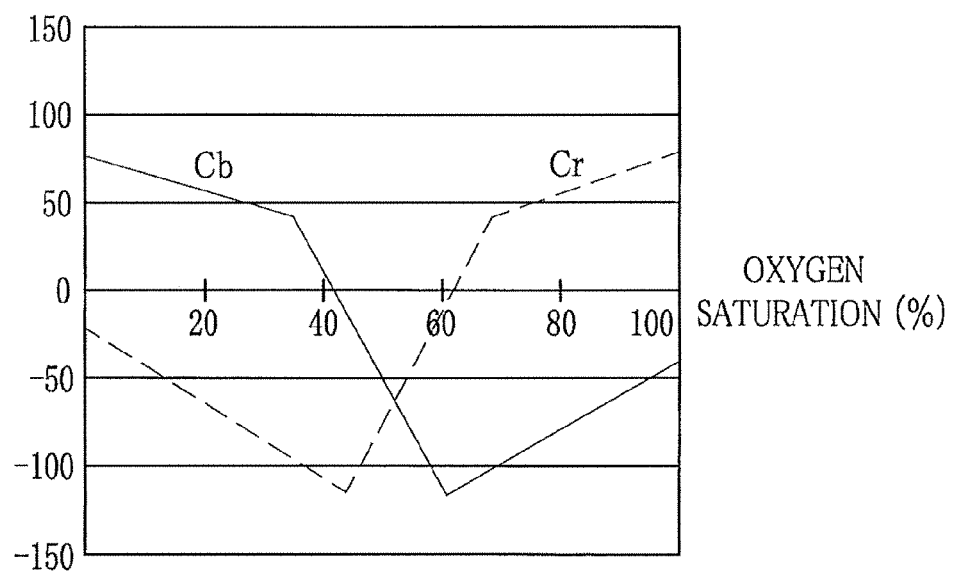
FIG. 12 is a graph showing a relation between the oxygen saturation and the color difference signals.

As shown in FIG. 12, in the color table 88a, when the oxygen saturation is high, a signal value of the color difference signal Cr is defined to be positive, while a signal value of the color difference signal Cb is defined to be negative. When the oxygen saturation is low, on the other hand, the signal value of the color difference signal Cr is defined to be negative, while the signal value of the color difference signal Cb is defined to be positive. When the oxygen saturation is at a medium level, a relationship in magnitude between the signal value of the color difference signal Cr and the signal value of the color difference signal Cb reverses. So, as the oxygen saturation increases, the hue or color of the oxygen saturation image changes from blue to light blue to green to yellow to orange to red.

Figure 13:
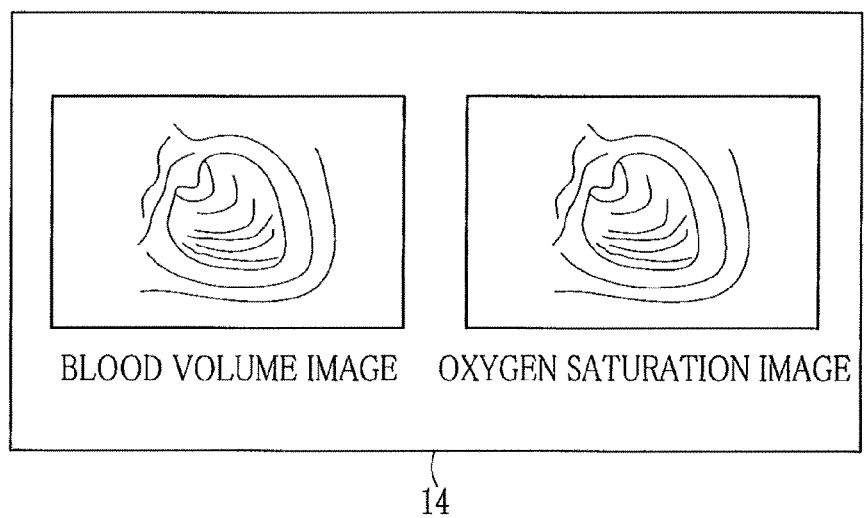
FIG. 13 shows a screen of a display device displaying a blood volume image and an oxygen saturation image side by side.
Figure 14:
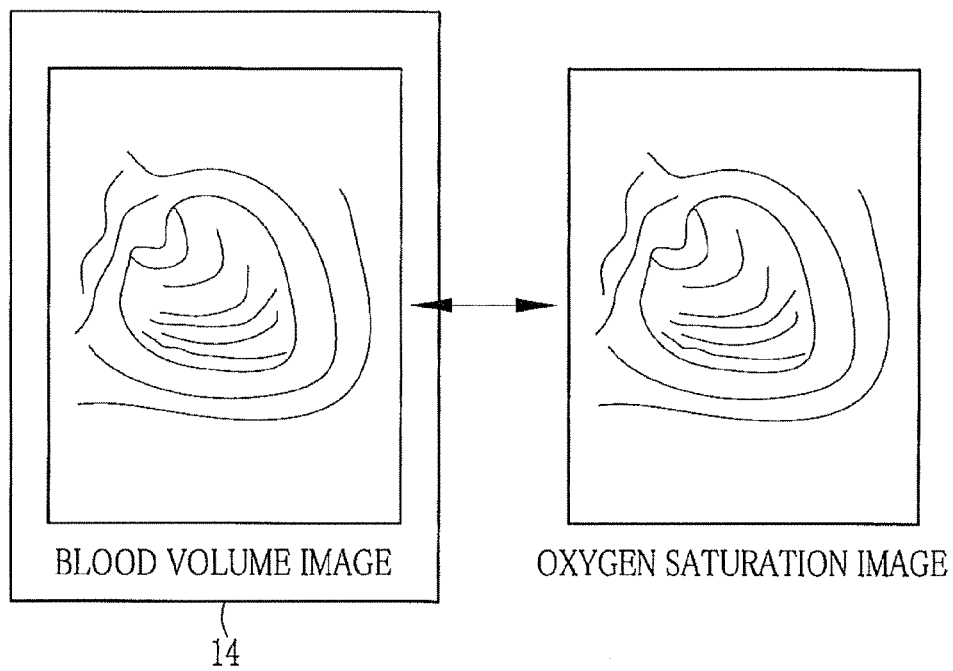
FIG. 14 shows the screen displaying one of the blood volume image and the oxygen saturation image.

The blood volume image and the oxygen saturation image generated are displayed on the display device 14. As shown in FIG. 13, the oxygen saturation image and the blood volume image may be displayed side by side simultaneously after their sizes are reduced. Alternatively, as shown in FIG. 14, a user may operate an image selecting means (not shown) provided in the input device 15 to select one of the oxygen saturation image and the blood volume image. The image selected is displayed on the display device 14. Using both the blood volume image and the oxygen saturation image for the endoscopic diagnosing improves the capability to diagnose a lesion, for example, undifferentiated early gastric cancer, showing a distinctive feature both in the oxygen saturation and the blood volume.

Figure 15:
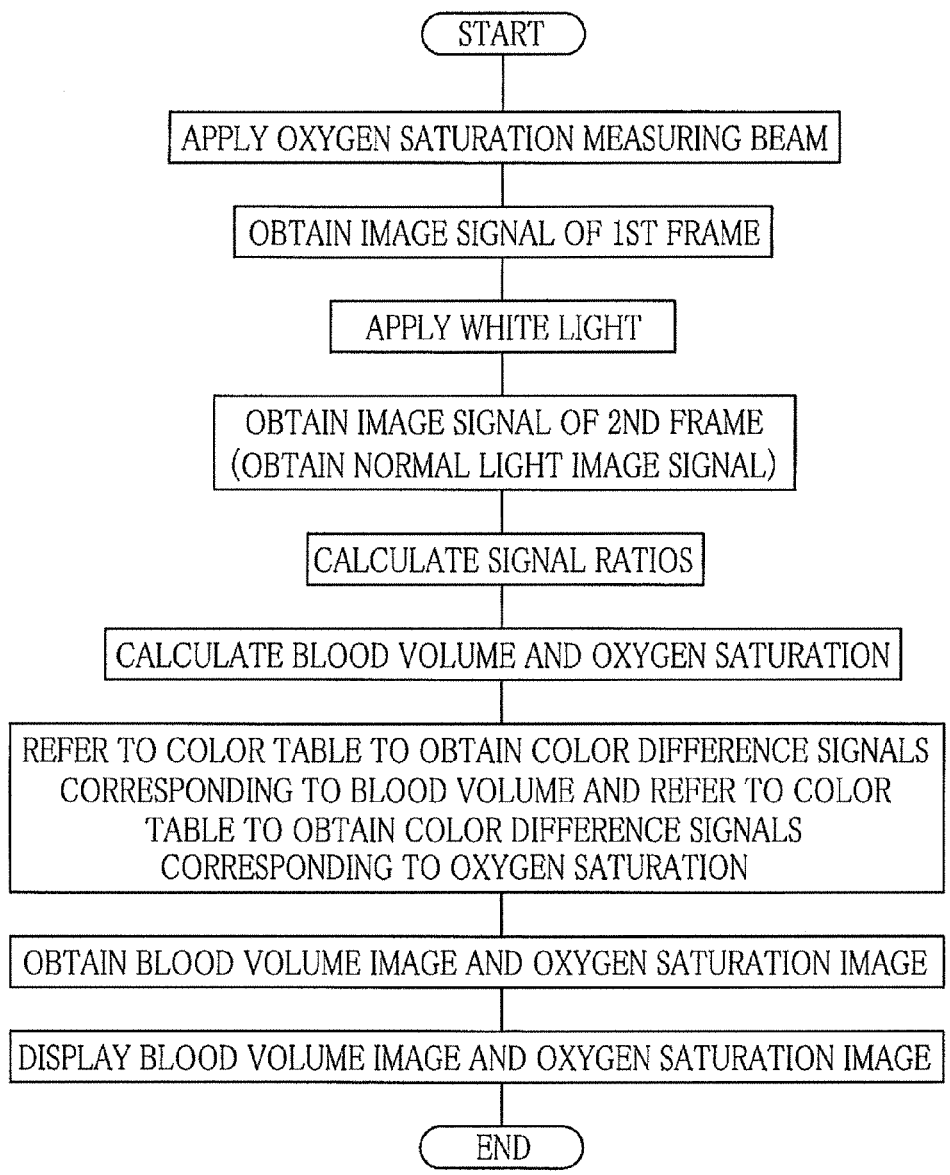
FIG. 15 is a flowchart showing steps for generating the blood volume image and the oxygen saturation image.
Figure 16:
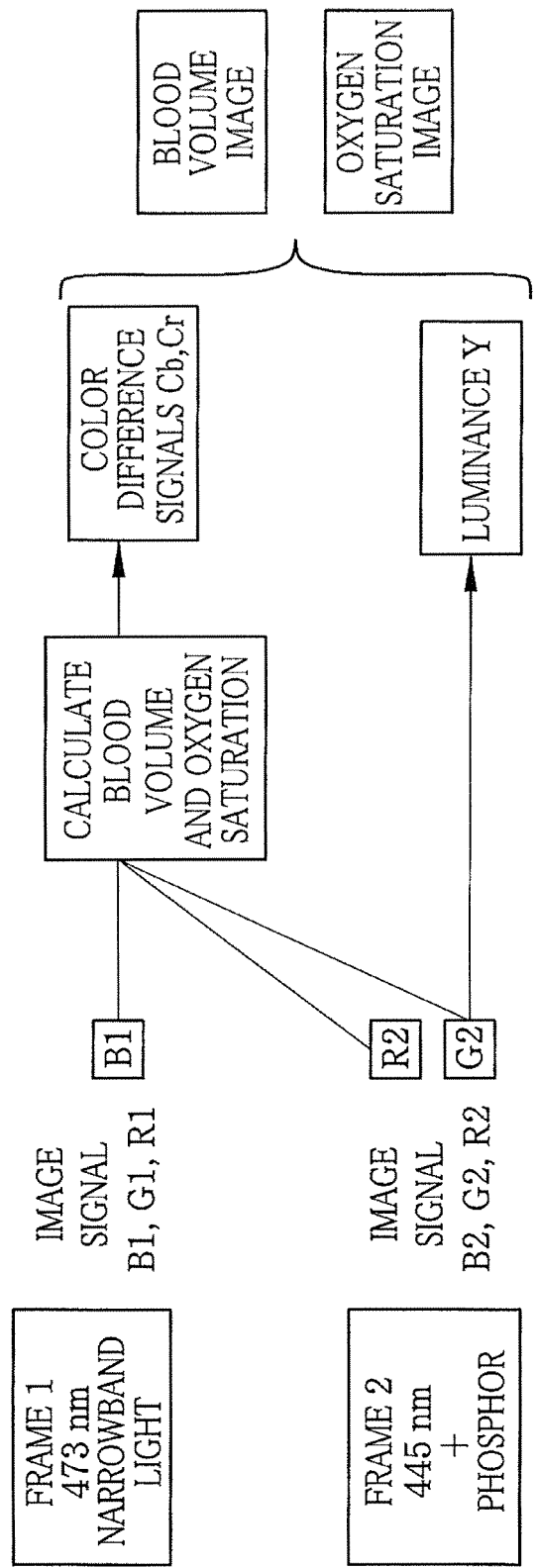
FIG. 16 is an explanatory view showing generation of the blood volume image and the oxygen saturation image.

Next, the operation of the present invention is described with reference to FIGS. 15 and 16. When the observation mode is switched to the functional information mode using the selection switch 17 of the endoscope apparatus 12, the narrowband oxygen saturation measuring beams at the center wavelength of 473 nm are applied from the distal portion 40 to the target portion of the subject. The light reflected from the target portion is captured by the image sensor 60. The image sensor 60 is a color CCD composed of B pixels, G pixels, and R pixels. Thereby, an image signal of a first frame is obtained. The image signal of the first frame is composed of a B signal B1, a G signal G1, and a R signal R1.

After the image signal of the first frame is obtained, the white light, generated by the excitation light at the center wavelength of 445 nm, is applied to the target portion of the subject through the distal portion 40. The image sensor 60 captures the light reflected from the target portion and the like. Thereby, an image signal (the normal light image signal) of a second frame is obtained. The image signal of the second frame is composed of a B signal B2, a G signal G2, and a R signal R2.

When the image signal of the second frame is obtained, the signal ratio calculator 84 obtains the signal ratios B1/G2 and R2/G2 between the image signal of the first frame and the image signal of the second frame, relative to the picture elements located at the same positions or coordinates in the first and second frames. The signal ratios are obtained for every picture element. Thereafter, based on the correlations stored in the correlation storage 85, the blood volume and the oxygen saturation calculator 86 obtains the blood volume corresponding to the signal ratio R2/G2 calculated by the signal ratio calculator 84. The blood volume and the oxygen saturation calculator 86 also obtains the oxygen saturation corresponding to the signal ratios B1/G2 and R2/G2 calculated by the signal ratio calculator 84. The blood volume and the oxygen saturation are obtained for every picture element.

When the blood volume and the oxygen saturation are obtained for each picture element, the color table 87a in the blood volume image generator 87 is referred to. Thereby, the color difference signals Cb and Cr corresponding to the blood volume are obtained. The blood volume image is generated based on the color difference signals Cb and Cr and the luminance Y. The G signal G2 of the normal light image signal is assigned to the luminance Y. The blood volume image shows the blood vessels in pseudo color in accordance with their blood volumes. Similarly, with the use of the color table 88a, the oxygen saturation image is generated. The oxygen saturation image shows the blood vessels in pseudo color in accordance with their oxygen saturations. The blood volume image and the oxygen saturation image are displayed on the display device 14.

Figure 17:
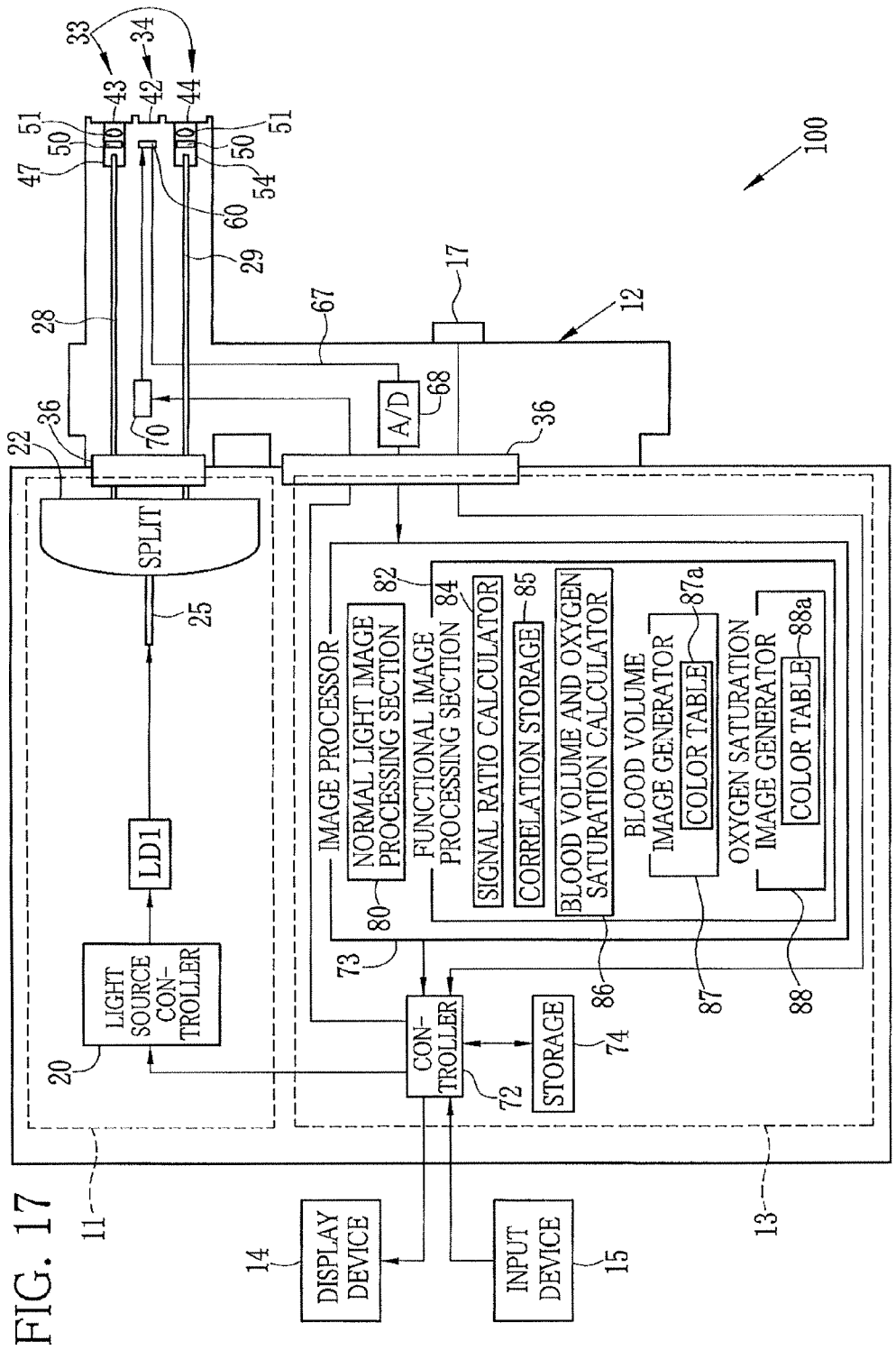
FIG. 17 is a block diagram showing a configuration of another endoscope system in the first embodiment.

In the first embodiment, the blood volume and the oxygen saturation are calculated using two frames of image signals. The image signal of the first frame is obtained by applying the narrowband light having the center wavelength of 473 nm. The image signal of the second frame is obtained by applying the white light. The white light is emitted from the phosphor being excited by the excitation light having the center wavelength of 445 nm. Alternatively, as shown in FIG. 17, the white light may be generated by applying the excitation light having the center wavelength of 473 nm, emitted from the laser light source LD1, to the phosphor 50. In this case, the blood volume and the oxygen saturation can be obtained from an image signal of a single frame captured while the white light is applied to the target portion of the subject. Unlike the endoscope system 10 using the four projection units 46, 47, 53, and 54 to apply the four paths of light beams, an endoscope system 100 shown in FIG. 17 applies two paths of light beams from the respective projection units 47 and 54.

In the image signal, the B signal B includes a signal corresponding to the excitation light having the center wavelength of 473 nm and a signal corresponding to a small amount of light out of the light from the phosphor being excited by the excitation light. The G signal G includes a signal corresponding to spectral illumination in a wavelength range mainly from 540 nm to 580 nm out of the light from the phosphor being excited. The R signal R includes a signal corresponding to spectral illumination in a wavelength range from 590 nm to 700 nm out of the light from the phosphor being excited and a signal corresponding to a small amount of the excitation light.

Accordingly, the signal ratio used for the calculation of the blood volume is R/G. The signal ratios used for the calculation of the oxygen saturation are B/G and R/G. The signal ratio R/G corresponds to the signal ratio R2/G2. The signal ratio B/G corresponds to the signal ratio B1/G2. Methods for calculating the blood volume and the oxygen saturation are similar to the above, so explanations thereof are omitted. To generate the pseudo-color blood volume image and the pseudo-color oxygen saturation image, the G signal G is assigned to the luminance.

Figure 18:
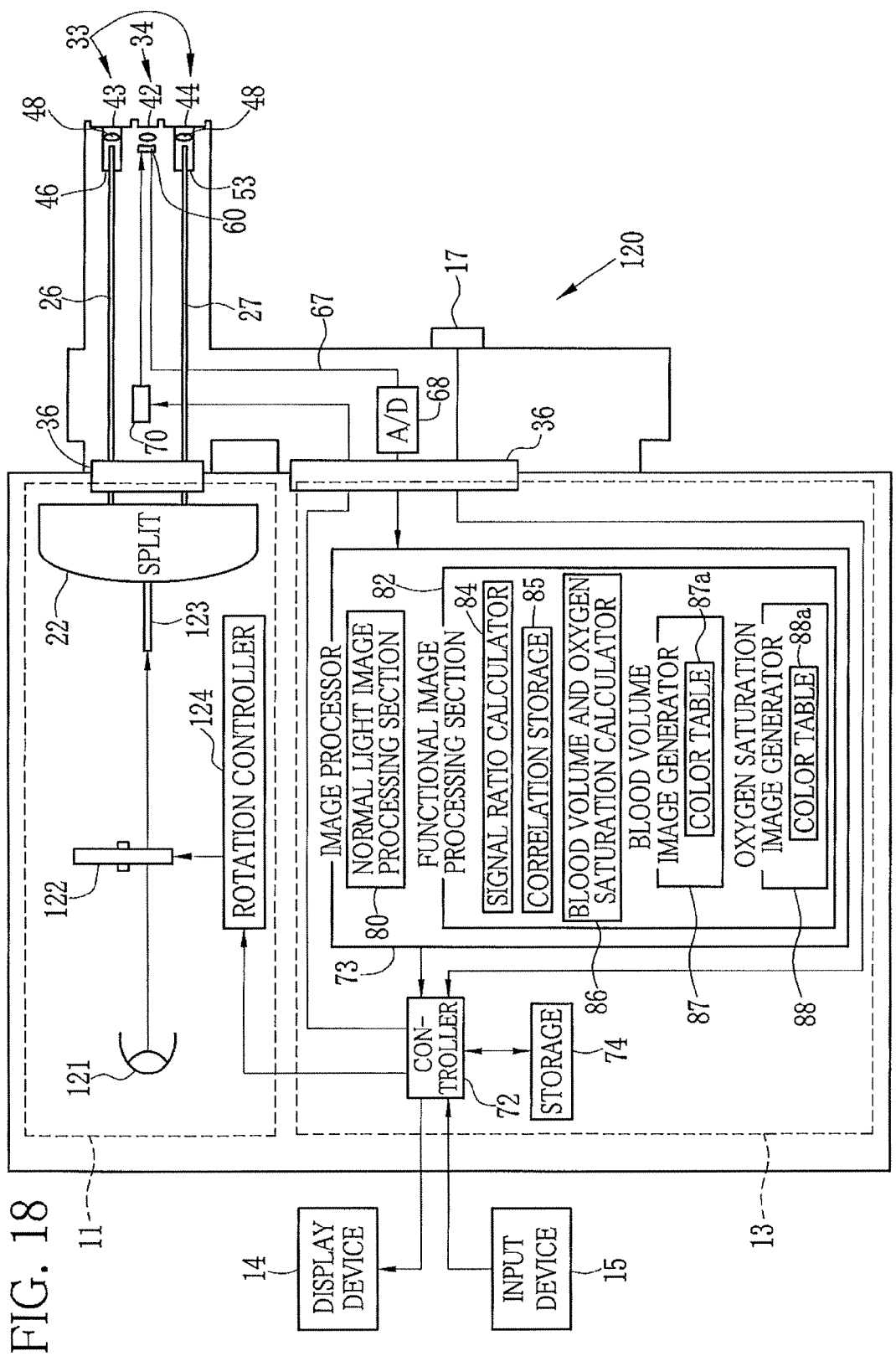
FIG. 18 is a block diagram showing a configuration of an endoscope system of a second embodiment.

As shown in FIG. 18, an endoscope system 120 of a second embodiment uses the light source apparatus 11 of a rotating-filter type. The endoscope system 120 is provided with a broadband light source 121, a rotating filter 122, an optical fiber 123, and a rotation controller 124. The broadband light source 121 is a xenon light source, for example, and emits white light having spectral intensity shown in FIG. 19. The rotating filter 122 allows the whole of the white light or a wavelength component of the oxygen saturation measuring beams out of the white light to pass therethrough. The light passed through the rotating filter 122 is incident on the optical fiber 123. The rotation controller 124 controls the rotation of the rotating filter 122. The light incident on the optical fiber 123 is split into two paths of light beams by the splitter 22. One of the two paths of light beams is applied from the projection unit 46 to the target portion of the subject through the light guide 26. The other path of the light beams is applied from the projection unit 53 to the target portion of the subject through the light guide 27. Remaining reference numerals denote parts similar to those in the endoscope system 10, so descriptions thereof are omitted.

Figure 20:
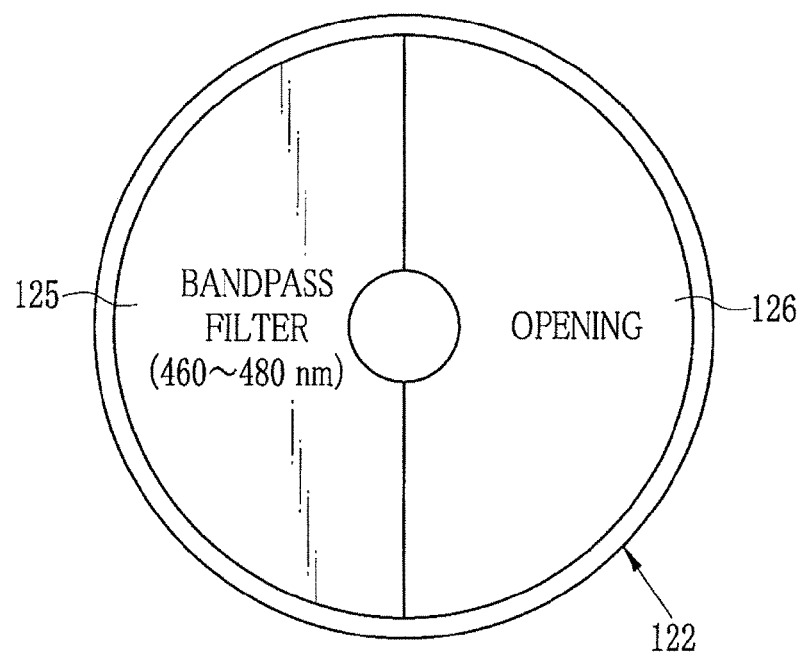
FIG. 20 is a front view of a rotating filter.

As shown in FIG. 20, the rotating filter 122 is provided with a bandpass filter 125 and an opening 126. Out of the white light, the bandpass filter 125 allows the oxygen saturation measuring beams (see FIG. 4) in the wavelength range from 460 nm to 480 nm to pass therethrough. The opening 126 allows the whole of white light to pass therethrough. By rotating the rotating filter 122, the oxygen saturation measuring beams and the white light are applied alternately to the target portion of the subject. Similar to the first embodiment, the image signal of the first frame is obtained when the oxygen saturation measuring beams are applied. The image signal of the second frame is obtained when the white light is applied. The oxygen saturation image is generated from the two frames of image signals in the similar manner to the first embodiment.

Figure 19:
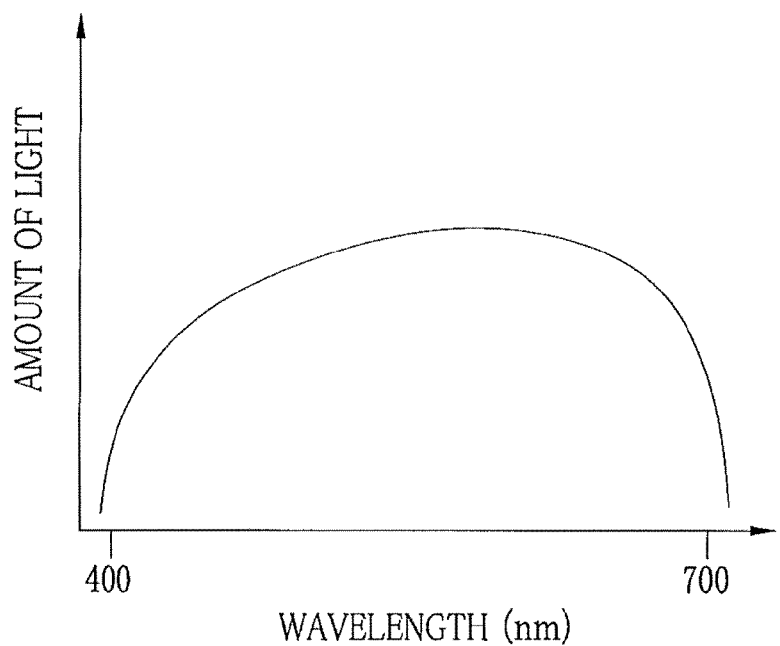
FIG. 19 is a graph showing an emission spectrum of the white light.

In the second embodiment, because the white light has the spectral intensity property shown in FIG. 19, the B signal B2 of the normal light image signal includes a signal of the light in the wavelength range from 400 nm to 530 nm. The G signal G2 includes a signal of the light in the wavelength range from 540 nm to 580 nm. The R signal R2 includes a signal of the light in the wavelength range from 590 nm to 700 nm. A method for calculating the blood volume and the oxygen saturation is similar to that of the first embodiment, so the descriptions thereof are omitted.

Figure 21:
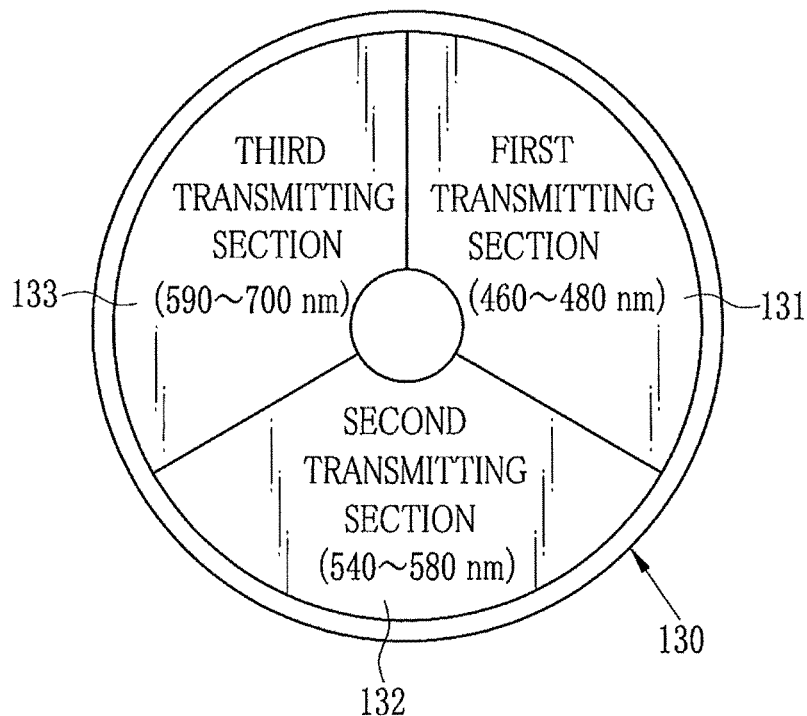
FIG. 21 is a front view of a rotating filter of another embodiment.

In the second embodiment, a rotating filter 130 shown in FIG. 21 may be used instead of the rotating filter 122 shown in FIG. 20. The rotating filter 130 is provided with first to third transmitting sections 131 to 133. Out of the white light from the broadband light source 121, the first transmitting section 131 allows first light beams to pass therethrough. The first light beams are in a wavelength range from 460 nm to 480 nm. Out of the white light, the second transmitting section 132 allows second light beams to pass therethrough. The second light beams are in a wavelength range from 540 nm to 580 nm. Out of the white light, the third transmitting section 133 allows third light beams to pass therethrough. The third light beams are in a wavelength range from 590 nm to 700 nm. When the rotating filter 130 is rotated, the first to third light beams are applied to the target portion of the subject successively and repeatedly.

When the rotating filter 130 is used, the monochrome image sensor 60 is used. The monochrome image sensor 60 captures an image every time the light beams, passed through the rotating filter 130, are applied. By the application of the first to third light beams, three frames of image signals are obtained, respectively. Out of the image signals, an image signal obtained when the first light beams are applied is defined as the B signal B. An image signal obtained when the second light beams are applied is defined as the G signal G. An image signal obtained when the third light beams are applied is defined as the R signal R.

Accordingly, the signal ratio used for the calculation of the blood volume is R/G. The signal ratios used for the calculation of the oxygen saturation are B/G and R/G. The signal ratio R/G corresponds to the signal ratio R2/G2 of the first embodiment. The signal ratio B/G corresponds to the signal ratio B1/G2 of the first embodiment. The method for calculating the blood volume and the oxygen saturation is similar to that of the first embodiment, so descriptions thereof are omitted. To generate the pseudo-color blood volume image and the pseudo-color oxygen saturation image, the G signal G is assigned to the luminance.

Figure 22:
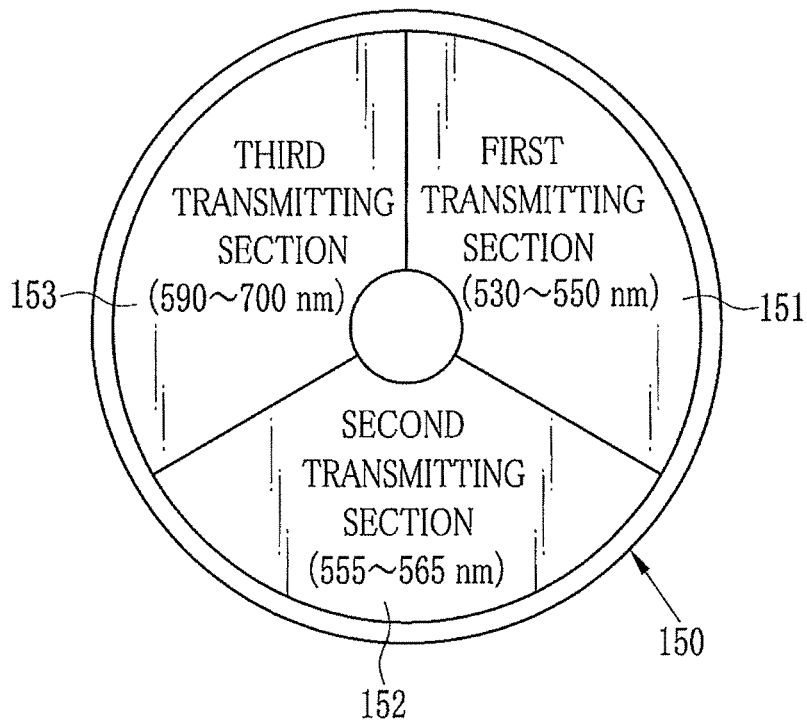
FIG. 22 is a front view of a rotating filter of further another embodiment.

In the second embodiment, a rotating filter 150 shown in FIG. 22 may be used instead of the rotating filter 130 shown in FIG. 21. The rotating filter 150 is provided with first to third transmitting sections 151 to 153. Out of the white light, the first transmitting section 151 of the rotating filter 150 allows first light beams to pass therethrough. The first light beams are in a wavelength range from 530 nm to 550 nm. The second transmitting section 152 allows second light beams to pass therethrough. The second light beams are in a wavelength range from 555 nm to 565 nm. The third transmitting section 153 allows third light beams to pass therethrough. The third light beams are in a wavelength range from 590 nm to 700 nm. When the rotating filter 150 is rotated, the first to third light beams are applied successively and repeatedly to the target portion of the subject.

When the rotating filter 150 is used, the color image sensor 60 captures an image every time first, second, or third light beams are applied. The first and second light beams are detected mainly by the G pixel of the image sensor 60. Accordingly, when the first and second light beams are applied, the G signals Ga and Gb are obtained as the image signals, respectively. On the other hand, the third light beams are detected mainly by the R pixel of the image sensor 60. Thereby, the R signal Rc is obtained as the image signal. Here, the image signals Ga and Rc are obtained from reflected light beams in the two respective wavelength ranges in each of which the absorption coefficient varies in accordance with a change in the oxygen saturation of hemoglobin in blood. The image signal Gb is obtained from the reflected light in a wavelength range in which the absorption coefficient is unchanged. Accordingly, the signal ratio Ga/Gb varies depending on the oxygen saturation and the blood volume. The signal ratio Rc/Gb varies depending mainly on the blood volume.

The signal ratio Rc/Gb is used for calculating the blood volume. The signal ratios Ga/Gb and Rc/Gb are used for calculating the oxygen saturation. The signal ratio Rc/Gb corresponds to the signal ratio R2/G2 of the first embodiment. The signal ratio Ga/Gb corresponds to the signal ratio B1/G2 of the first embodiment. The method for calculating the blood volume and the oxygen saturation is similar to that in the first embodiment, so descriptions thereof are omitted. To generate the pseudo-color blood volume image and the pseudo-color oxygen saturation image, the G signal Ga or Gb is assigned to the luminance.

Figure 23:
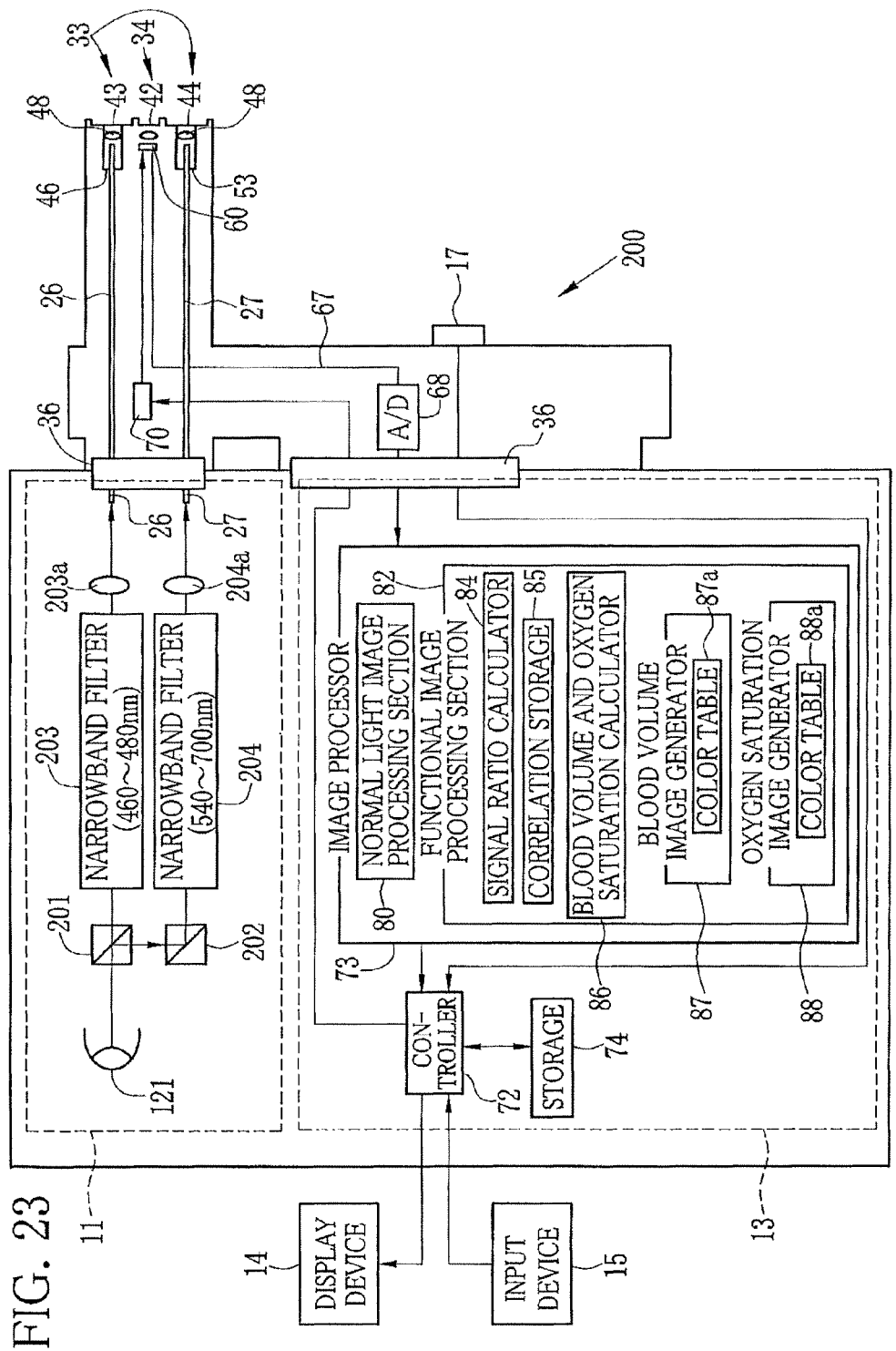
FIG. 23 is a block diagram showing a configuration of an endoscope system of a third embodiment.

As shown in FIG. 23, instead of the rotating filter 122 shown in the second embodiment, an endoscope system 200 of a third embodiment uses a half prism 201, a reflection prism 202, and narrowband filters 203 and 204 to generate the light beams used for calculating the blood volume and the oxygen saturation. Remaining reference numerals denote parts similar to those of the endoscope system 120 in the second embodiment.

In the light source apparatus 11, the half prism 201 splits the white light, emitted from the broadband light source 121, into two paths of light beams. One of the two paths of the light beams is incident on the narrowband filter 203. The other path of the light beams is reflected by the reflection prism 202 and then incident on the narrowband filter 204. Out of the white light, the narrowband filter 203 allows the light beams in a wavelength range from 460 nm to 480 nm to pass therethrough. The narrowband filter 204 allows the light beams in a wavelength range from 540 nm to 700 nm to pass therethrough. The light beams passed through the narrowband filter 203 are applied to the target portion of the subject through a lens 203a and the light guide 26. The light beams passed through the narrowband filter 204 are applied to the target portion of the subject through a lens 204a and the light guide 27. The light beams passed through the narrowband filters 203 and 204 are applied simultaneously to the target portion of the subject.

To capture an image of the target portion of the subject, the color image sensor 60 is used in the similar manner to the first embodiment. Accordingly, in the image signal obtained by the image capture, the B signal B includes a signal corresponding to the light beams in the wavelength range from 460 nm to 480 nm. The G signal G includes a signal corresponding to the light beams in the wavelength range from 540 nm to 580 nm. The R signal R includes a signal corresponding to the light beams in the wavelength range from 590 nm to 700 nm.

Accordingly, the signal ratio R/G is used for calculating the blood volume. The signal ratios B/G and R/G are used for calculating the oxygen saturation. The signal ratio R/G corresponds to the signal ratio R2/G2 of the first embodiment. The signal ratio B/G corresponds to the signal ratio B1/G2 of the first embodiment. A method for calculating the blood volume and the oxygen saturation is similar to that of the first embodiment, so descriptions thereof are omitted. To generate the pseudo-color blood volume image and the pseudo-color oxygen saturation image, the G signal G is assigned to the luminance.

In the above embodiment, in generating the blood volume image and the oxygen saturation image, the information on the blood volume and on the oxygen saturation is expressed in pseudo color. Alternatively, the information on the blood volume and on the oxygen saturation may be expressed in monochrome gradation.

Various changes and modifications are possible in the present invention and may be understood to be within the present invention.

What is claimed is:

1. An endoscope system comprising:
   an illuminating section for projecting illumination light to a portion to be observed, the portion including a blood vessel;
   an image signal obtaining section for obtaining first to third image signals from reflection light reflected from the portion, the reflection light being in a wavelength range from 460 nm to 700 nm, the first image signal being obtained from first reflection light including a wavelength range in which an absorption coefficient varies in accordance with oxygen saturation of hemoglobin in blood, the second image signal being obtained from second reflection light including a wavelength range in which an absorption coefficient varies in accordance with blood volume, the third image signal being obtained from third reflection light including an arbitrary wavelength range;
   a blood volume and oxygen saturation calculating section for obtaining information on the blood volume and on the oxygen saturation based on the first to third image signals;
   a first color table for blood volume which stores a relation between blood volume and signal value of a color difference signal;
   a second color table for oxygen saturation which stores a relation between oxygen saturation and signal value of a color difference signal;
   a blood volume and oxygen saturation image generator for generating a blood volume image and an oxygen saturation image, the blood volume image representing the information on the blood volume, the oxygen saturation image representing the information on the oxygen saturation, the blood volume image comprising luminance to which the third image signal is assigned and color difference signal to which signal value of the color difference signal corresponding to blood volume which is obtained at the blood volume and oxygen saturation calculating section in the first color table, the oxygen saturation image comprising luminance to which the third image signal is assigned and color difference signal to which signal value of the color difference signal corresponding to oxygen saturation which is obtained at the blood volume and oxygen saturation calculating section in the second color table; and
   a display section for displaying the blood volume image and the oxygen saturation image simultaneously or selectively.

2. The endoscope system of claim 1, wherein the color variation of the blood volume image by change of the blood volume is different from the color variation of the oxygen saturation image by change of the oxygen saturation.

3. The endoscope system of claim 1, wherein one of the first and second color tables varies in chroma and the other varies in hue.

4. The endoscope system of claim 1, wherein the blood volume and oxygen saturation calculating section calculates the blood volume-independent oxygen saturation which is not dependent on the blood volume.

5. The endoscope system of claim 4, wherein the blood volume and oxygen saturation obtaining section includes:
   a signal ratio calculator for obtaining a first signal ratio and a second signal ratio based on the first to third image signals, and the first signal ratio being a ratio of the second image signal and the third image signal, the second signal ratio being a ratio of the first image signal and the third image signal;
   a correlation storage for storing a first correlation between the blood volume and the first signal ratio and a second correlation between the oxygen saturation and the first and second signal ratios; and
   a calculator for obtaining the information on the blood volume from the first correlation and the information on the oxygen saturation from the second correlation, and the blood volume corresponds to the first signal ratio, and the blood volume-independent oxygen saturation corresponds to the first and second signal ratio.

6. The endoscope system of claim 5, wherein the first reflection light is blue reflection light including a wavelength range from 460 nm to 480 nm, and the second reflection light is red reflection light including a wavelength range from 590 nm to 700 nm.

7. The endoscope system of claim 6, wherein the illuminating section projects white light as the illumination light to the portion and the image signal obtaining section images the portion with a color image sensor provided with R, G, and B color filters on its imaging surface, to obtain the first to third image signals.

8. The endoscope system of claim 7, wherein the white light comprises pseudo white light generated by applying excitation light having a predetermined wavelength to a phosphor.

9. The endoscope system of claim 6, wherein the illuminating section successively projects light in a wavelength range from 460 nm to 480 nm, light in a wavelength range from 540 nm to 580 nm, and light in a wavelength range from 590 nm to 700 nm as the illumination light.

10. The endoscope system of claim 9, wherein the light in each of the wavelength ranges is generated by filtering white light with a narrowband filter.

11. The endoscope system of claim 6, wherein the illuminating section simultaneously projects light in a wavelength range from 460 nm to 480 nm and light in a wavelength range from 540 nm to 700 nm as the illumination light, and the image signal obtaining section images the portion with a color image sensor provided with R, G, and B color filters on its imaging surface.

12. The endoscope system of claim 5, wherein the illuminating section projects light, having a wavelength range in which the absorption coefficient varies in accordance with a change in the oxygen saturation of hemoglobin in blood, as the illumination light to the portion to obtain the first image signal, and the illuminating section projects white light as the illumination light and the image signal obtaining section images the portion with a color image sensor provided with R, G, and B color filters on its imaging surface, to obtain the second and third image signals.

13. The endoscope system of claim 12, wherein the white light comprises pseudo white light generated by applying excitation light having a predetermined wavelength to a phosphor.

14. The endoscope system of claim 5, wherein the illuminating section successively projects light in a wavelength range from 530 nm to 550 nm, light in a wavelength range from 555 nm to 565 nm, and light in a wavelength range from 590 nm to 700 nm as the illumination light, and the image signal obtaining section images the portion with a color image sensor provided with R, G, and B color filters on its imaging surface.

15. The endoscope system of claim 14, wherein the light in each of the wavelength ranges is generated by filtering white light with a narrowband filter.

16. The endoscope system of claim 1, wherein the third reflection light is green reflection light including a wavelength range from 540 nm to 580 nm.

17. A processor apparatus used with an endoscope, the endoscope having an image signal obtaining section for obtaining first to third image signals from reflection light reflected from a portion to be observed, the portion including a blood vessel, the reflection light being in a wavelength range from 460 nm to 700 nm, the first image signal being obtained from first reflection light including a wavelength range in which an absorption coefficient varies in accordance with oxygen saturation of hemoglobin in blood, the second image signal being obtained from second reflection light including a wavelength range in which an absorption coefficient varies in accordance with blood volume, the third image signal being obtained from third reflection light including an arbitrary wavelength range; the processor apparatus including:
- a receiving section for receiving the first to third image signals from the endoscope;
- a blood volume and oxygen saturation calculating section for obtaining information on the blood volume and on the oxygen saturation based on the first to third image signals;
- a first color table for blood volume which stores a relation between blood volume and signal value of a color difference signal;
- a second color table for oxygen saturation which stores a relation between oxygen saturation and signal value of a color difference signal; and
- a blood volume and oxygen saturation image generator for generating a blood volume image and an oxygen saturation image, the blood volume image representing the information on the blood volume, the oxygen saturation image representing the information on the oxygen saturation, the blood volume image comprising luminance to which the third image signal is assigned and color difference signal to which signal value of the color difference signal corresponding to blood volume which is obtained at the blood volume and oxygen saturation calculating section in the first color table, the oxygen saturation image comprising luminance to which the third image signal is assigned and color difference signal to which signal value of the color difference signal corresponding to blood volume which is obtained at the oxygen saturation and oxygen saturation calculating section in the second color table.

18. A method for generating images comprising:
- projecting illumination light to a portion to be observed, the portion including a blood vessel;
- obtaining first to third image signals from reflection light reflected from the portion, the reflection light being in a wavelength range from 460 nm to 700 nm, the first image signal being obtained from first reflection light including a wavelength range in which an absorption coefficient varies in accordance with oxygen saturation of hemoglobin in blood, the second image signal being obtained from second reflection light including a wavelength range in which an absorption coefficient varies in accordance with blood volume, the third image signal being obtained from third reflection light including an arbitrary wavelength range;
- obtaining information on the blood volume and on the oxygen saturation based on the first to third image signals;
- storing a relation between blood volume and signal value of a color difference signal in a first color table for blood volume;
- storing a relation between oxygen saturation and signal value of a color difference signal in a second color table for oxygen saturation; and
- generating a blood volume image and an oxygen saturation image, the blood volume image representing the information on the blood volume, the oxygen saturation image representing the information on the oxygen saturation, the blood volume image comprising luminance to which the third image signal is assigned and color difference signal to which signal value of the color difference signal corresponding to blood volume which is obtained at the blood volume and oxygen saturation calculating section in the first color table, the oxygen saturation image comprising luminance to which the third image signal is assigned and color difference signal to which signal value of the color difference signal corresponding to oxygen saturation which is obtained at the blood volume and oxygen saturation calculating section in the second color table.

* * * * *